US006626355B2

(12) United States Patent
Sasse et al.

(10) Patent No.: US 6,626,355 B2
(45) Date of Patent: Sep. 30, 2003

(54) MEDICAL DEVICE

(75) Inventors: Joachim Sasse, Glienicke (DE); Matthias Stiller, Potsdam (DE)

(73) Assignee: W.O.M. World of Medicine GmbH (DE)

( * ) Notice: Subject to any disclaimer, the term of this patent is extended or adjusted under 35 U.S.C. 154(b) by 99 days.

(21) Appl. No.: 09/778,615

(22) Filed: Feb. 7, 2001

(65) Prior Publication Data

US 2001/0020148 A1 Sep. 6, 2001

(30) Foreign Application Priority Data

Feb. 7, 2000 (DE) .......................... 100 05 108

(51) Int. Cl.[7] .............................................. G06F 17/00
(52) U.S. Cl. ...................... 235/375; 235/449; 235/451; 235/382
(58) Field of Search ................................. 235/375, 382, 235/441, 449, 451, 492, 493; 604/34

(56) References Cited

U.S. PATENT DOCUMENTS

| | | | | |
|---|---|---|---|---|
| 4,187,057 A | * | 2/1980 | Xanthopoulos | 417/477.11 |
| 4,479,762 A | * | 10/1984 | Bilstad et al. | 206/364 |
| 5,078,683 A | * | 1/1992 | Sancoff et al. | 128/DIG. 13 |
| 5,230,614 A | * | 7/1993 | Zanger et al. | 417/477.9 |
| 5,679,945 A | * | 10/1997 | Renner et al. | 235/441 |
| 5,920,054 A | * | 7/1999 | Uber, III | 235/375 |
| 6,411,199 B1 | * | 6/2002 | Geiszler et al. | 340/10.1 |

* cited by examiner

Primary Examiner—Michael G. Lee
Assistant Examiner—Steven S. Paik
(74) Attorney, Agent, or Firm—McGlew and Tuttle, P.C.

(57) ABSTRACT

A medical device with a medical apparatus (2) includes an accessory port, and with at least one accessory piece (1) having a connection element that is complementary to the accessory port. The connection element includes a storage unit where coded identification information is stored. With accessory piece (1) connected to device (2) coded or un-coded identification information is readable by a readout unit disposed in the section of the accessory port. In the case of reading coded identification information, de-codable, read-out and de-coded identification information is compared to identification information stored in readout unit. The medical device is activated when the identification information matches the desired identification information. The device is blocked when the identification information does not match. The coded identification information is de-coded by means of a proprietary key code.

17 Claims, 3 Drawing Sheets

MEDICAL DEVICE

FIELD OF THE INVENTION

The invention relates to a medical device with a medical apparatus comprising an accessory port, and with at least one accessory piece comprising a connection element being complementary to said accessory port, the connection element carrying identification information, with said accessory piece connected to the device said identification information being readable by a readout unit located at said accessory port, read and de-coded identification information being compared to preset identification information stored in said readout unit, and the medical device being activated if the identification information match the preset identification information, and being blocked if the identification information do not match. Medical devices in the meaning of the invention are in particular sucking and/or rinsing pumps or gas supply systems for dialysis, arthroscopy, hyteroscopy, cystoscopy, laparoscopy and breathing technologies. An accessory piece typically is a hose set and/or a filter, for instance a pump hose set for roller pumps, gas hose sets, if applicable with a sterile filter and/or a heating device for a medium passing through, for the connection of the medical device to a medical instrument for said applications. A number of functional accessory pieces may be provided for a device, and it is understood that when using one single device or one single device type, sufficient compatibility between the respective connection element and the accessory port exists.

BACKGROUND OF THE INVENTION

A medical device of the type mentioned above is known as an internal state of the art. Herein, identification information are stored as a bar code and are read out by means of a bar code reader. The structure of bar codes is well known and standardized, so that any user can read a bar code. Insofar a usual bar code does not provide coded identification information; the identification information is available like text in the clear.

Normally, accessory pieces are diposable articles, which are suitable for a limited number of applications only. Typically, many accessory pieces, such as hose sets, are; once-only articles, for sterility reasons. There are therefore general problems for medical devices in that accessory pieces could inadmissibly be re-used, for cost reasons. Another problem is that there are suppliers of accessory pieces, and only of accessory pieces, whose products do not meet) all requirements, in technical or in medical respect. This will lead to substantial health risks for patients, which is of course very disturbing.

The above problems have been solved by authorized manufacturers of accessory pieces in various ways. When using a bar code, the bar code scanner reads the bar code and verifies whether the read bar code corresponds to a reference list of allowed bar codes. If yes, an activation of the device is possible; if not, there is no activation possible. This internal state of the art is a progress for the solution of the above problems, however it is relatively easy to circumvent the thus established safety function. An imitator only needs to read out the bar code and apply it on his products of minor quality.

A different approach to solve the mentioned problems is a complicated shaping of accessory port and connection element. This will make unauthorized imitations more difficult to produce, will however also lead to substantial higher costs for authorized manufacturers, with the consequence of higher prices for the accessory pieces. Finally, no advantage will be achieved, since an unauthorized imitator can nevertheless work on relatively low cost by medically concerning savings in the fields of the technical properties or for instance of sterility.

Further problems in conjunction with accessory pieces will be the often relatively limited durability and the therewith connected expiry dates and the possible mis-use by exceeding the maximum allowable application cycles (typically 1 for hose sets). This is in no way solved by the measures described above.

SUMMARY OF THE INVENTION

The invention is therefore based on the technical object to provide a medical device excluding dangers to patients by using inadmissible accessory pieces. Another embodiment of the invention is based on the further technical object to exclude dangers to patients by inadmissible multiple uses of accessory pieces or by using accessory pieces the expiry dates of which have been exceeded.

For achieving the first object, the invention provides a medical device with a medical apparatus comprising an accessory port, and with at least one accessory piece comprising a connection element being complementary to the accessory port, the connection element including a storage unit where coded identification information, with the accessory piece connected to the device coded or un-coded identification information being readable by means of a readout unit disposed in the section of the accessory port and, in the case of reading of coded identification information, being de-codable, read and de-coded identification information being compared to identification information stored in said readout unit, and the medical device being activated when the identification information at least partly match the desired identification information, and being blocked when the identification information do not match, and coded identification information being de-codable by means of a proprietary key code. It is understood, when reading out as un-coded identification information, that then a de-coding has to be performed beforehand in the storage unit. As a storage unit, any device for fixing information is designated. These are in particular electronic, magnetic, and optical storage media. For the purpose of the invention, a storage unit may include components in addition to the basic memory, as for instance processors and/or communication assemblies. A readout unit typically comprises, in addition to the communication assemblies required for readout, also electronic means for processing the read-out identification information, in particular for comparing to the preset (valid) identification information and for controlling the device according to the result of such comparison. Identification information includes sequences of characters processed according to the structure of the basic memory, these sequences being characteristic for a certain type of an accessory piece and possibly also for an individual accessory piece, and being specified by an authorized manufacturer. In case the identification information is individually characterizing, it is recommended to subdivide the identification information into accessory piece type information and individual piece information. Then the comparison to the preset (valid) identification information will typically be performed with the accessory piece type information only. The authorized manufacturer will then also provide for the integration of respective identification information or accessory piece type information as preset (valid) identification information in the readout unit. Coded identification information differs from un-coded identification information in that the un-coded identification information has been transformed by means of the key code. On a binary basis, a coding may for instance in the simplest case be implemented by shifting the bit orders by means of a shift register function on the basis of, e.g. ASCII, characters, for instance mathematical operations with regard to the alphanumerical (alphabetical) order may be needed. Many various coding techniques are well known to the man skilled in the art and need not be explained here in more detail. Coded identification information in the meaning of the invention does however also exist, if the identification information are per se stored in clear in a storage unit, readout of the storage unit being however only possible by means of a key code or not being re-readable (so-called hidden information).

It is achieved by the invention, based on the identification information being present in the storage unit in a coded way and on the proprietary key required for de-coding (in the storage unit or the readout unit), that an imitation also of the storage unit including identification information permitting a setting into operation of the device is virtually impossible, at least however made considerably more difficult. Since only authorized manufacturers for accessory pieces will receive the proprietary key code, setting into operation of the device is only possible with admissible accessory pieces.

When connecting not admissible accessory pieces, setting into operation is however blocked, and it is recommended then to activate an alarm signal, usually visual or acoustic, in order to indicate the inadmissible accessory piece.

For the invention, in particular the following three embodiments are preferred. Firstly, decoding of identification information can be achieved by the readout unit transmits the key code to the storage unit, and that the storage unit enabling the identification information in an un-coded manner for readout, if the transmitted key code matches a key code stored in the storage unit. Then the identification information can be stored in the storage unit in clear, i.e. basically un-coded. Secondly, decoding of identification information can be achieved by the readout unit transmitting the key code to the storage unit, and in the storage unit a transformation of the coded identification information into un-coded identification information being performed by means of the key code then a readout of the un-coded identification information is performed. Thirdly, decoding of identification information can be achieved by the coded identification information being read out from the storage unit, and in the readout unit a transformation of the coded identification information into un-coded identification information being performed by means of the key code.

Of independent importance is another embodiment of the invention, wherein, possibly independent from the above features, the readout unit (additionally) reads out an expiry date stored in the storage unit and compares this to the date available as a real time value in the readout unit, and blocks the device on the day of readout once the expiry date is exceeded, and/or wherein identification information is individualizing for an accessory piece and the readout unit, beginning at the first-time connection (or separation) of the accessory piece detects the number of application cycles, related to the individual piece information, and blocks the device when the maximum admissible number of application cycles is exceeded. In detail, the latter can be achieved by that the read-out accessory piece type information in the readout unit being compared to a table stored in the readout unit, the elements of such table being different accessory piece type information and assigned maximum numbers of application cycles. After a determination of the maximum number of application cycles of the connected type of accessory piece, then for the also read-out and stored individual piece information, a comparison of the actual and the maximum number of application cycles will take place in the readout unit. In a preferred variant, the storage unit will however include a first storage section where the maximum number of application cycles are stored, and a second storage section where the actual number of application cycles are stored, the contents of the second storage section being increased by one at each connection (or also separation) and a comparison of both values taking place in the storage unit or the evaluation unit (after readout of both values). The essential element of this embodiment is therefore that the readout unit can also write into the storage unit, i.e. build up information in the storage element or modify it. Other variants are of course also possible.

By this embodiment, it is achieved that for instance disposable articles, such as disposable hose sets, will not be used several times, or that hose sets for multiple use are subjected to the given number of application cycles only. Further, utilization of a per se admissible accessory piece can be prevented, if its expiry date has been exceeded.

The key code and the processing thereof or the transformation of the coded identification information may be configured in any usual way. It is for instance possible that the key code is selected from the group including "fixed code, changing code, sequential changing code, stochastic changing code, and combination of such codes". In a fixed code, the key code is static. In a sequential changing code, the key code is replaced after each application by a subsequent new code. Subsequent may be serial key codes (e.g. serial numbers or real time). Herein is also included a pre-selected sequence of key codes of a given key code group with possibly cyclical selection, this codes having no internal relationship. Stochastic changing codes are modified in a random manner at least in part after each application. In all changing codes, it is understood that synchronism between readout unit and storage unit is required. Changing codes prevent mis-use for instance by undesired "tapping" of the key code at the occasion of a readout or other transmission of information between the readout and storage units.

In detail, a device according to the invention may be adapted in various ways. It is possible that the storage unit is configured as a transponder, and the readout unit as a transponder scanning transceiver. A transponder is an electronic circuitry which upon reception of a signal in turn will transmit a signal. A transponder scanning transceiver is an electronic circuitry which is adapted to the transmission of a signal activating a transponder and to the reception of a transponder signal. The terms "transmission" and "reception" are used here in a very broad sense. Transmission of information (among other data, key code, identification information etc.) between transponder and transponder scanning transceiver may take place by means of electromagnetic waves or inductively or capacitively or galvanically. Electro-magnetic waves are in particular radio waves (usually FM, VHF or UHF waves) and light waves (for instance IR, visible, UV). The relevant technologies are very well known and need not be explained here in more detail. A galvanic transmission of information is performed by groups of contacts contacted with contact fields (chip card technology). It is recommendable to also transmit, with the transmission of information from a transponder scanning transceiver to the transponder, the power required for operating the transponder. Then the transponder will not need an own power supply, and the disposal problems connected with batteries are avoided.

In a particularly simple embodiment of the invention, the storage unit is configured as a passive storage unit, having in particular magnetic stripes. Passive means that the storage unit cannot itself perform a transmission of information, but can rather only be read out and/or written on. This embodiment is particularly economical to make. However, the achievable degree of safety is lower than for active storage units, as described above.

Identification information may also contain a customer code, thus exchange of accessory pieces being prevented.

The invention further relates to a method for operating a medical device according to the invention, wherein after connection of an accessory piece to the device the identification information stored in the storage unit are read out, read-out and de-coded identification information being compared to identification information stored in the readout unit, and the medical device being activated when the identification information at least partly match the desired identification information, and being blocked when the identification information do not match. For this method, above explanations apply in a corresponding manner. Finally, the invention also relates to (digital) programs coding for the functions of the storage unit and for the functions of the readout unit according to the method according to the invention. When programmed logic and/or processors are used, it is recommendable that the processing software cannot be read back, thus the generation of doubles being prevented.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

Referring to the drawings in particular, in FIG. 1 a hose cassette 1 is shown for a peristaltic pump 2 (see also FIG. 2) with a cassette housing 3, a flexible hose 4 extending through cassette housing 3. The flexible hose 9 is guided in the cassette housing 3 along a circular segment, in the example shown approx. 180°. The cassette housing 3 has a substantially half-oval shape with two plane half-oval surfaces. One of the half-oval surface is closed and the opposite half-oval surface is open and thus comprises a cutout 5 for engagement of a roller wheel 6. The roller wheel 6 of the peristaltic pump 2 engages with a mounted hose cassette 1 into the interior of the circular segment. Connection elements 7, 8 for the connection of cassette housing 3 to peristaltic pump 2 can further be seen in FIG. 1. In FIG 2 an outside wall 22 of pump housing 21 is shown carrying the roller wheel 6. Connection elements 23, 34 are provided that are complementary to connection elements 7, 8 of the cassette. FIG. 2 also shows the roller wheel 6 projecting beyond outside wall 22 of the pump housing. With mounted hose cassette 1 mounted, the axis of rotation is substantially co-axial with the circular segment of the guiding mechanism of the hose 4 in cassette housing 3, as a comparison of FIGS. 1 and 2 will show.

Figure 1:
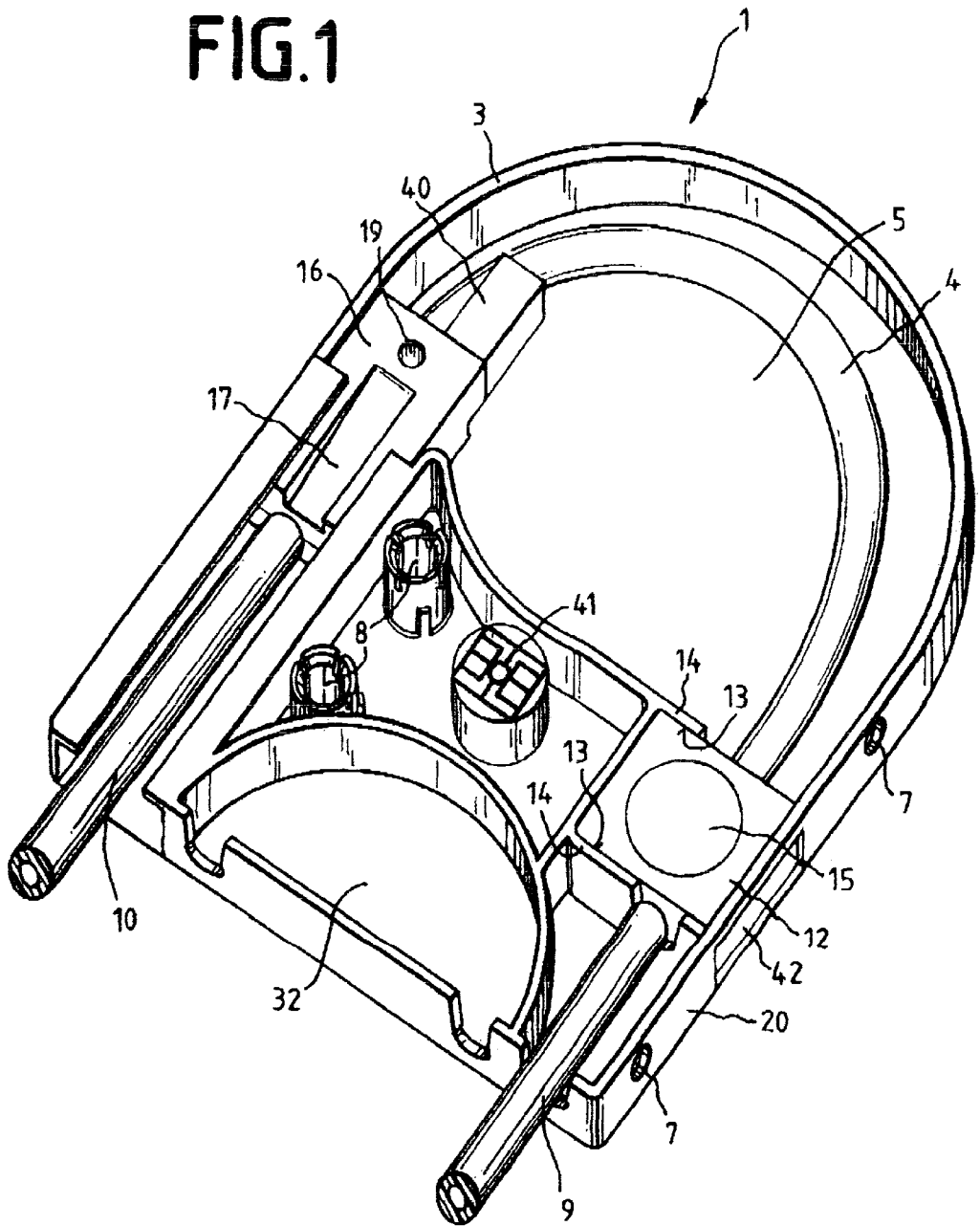
FIG. 1 is a partial view of an accessory piece.

From FIG. 1 can be appreciated that a hose leg 10 connected to the circular segment is displaceably supported between a mounting position and an operating position. The operating position is shown. It can be seen that a connection element 16 with a latch element is provided in the frame of the displaceable hose leg 10. The latch element comprises a stop surface 17. By means of this stop surface 17, for a cassette 1 mounted at peristaltic pump 2, a locking pin is lifted against spring pressure from a rest position during the displacement of displaceable hose leg 10 from the mounting position into the operating position. The latch element comprises in the direction of the operating position adjacent to stop surface 17 a blocking surface, behind which the locking element will engage in its locking position. A switching element is provided in the frame of peristaltic pump 2. This switching element interacting with the locking pin. The locking pin may, in its rest position, extend beyond its locking position from outside wall 22 of the pump housing 21, under the action of the force of a compression spring. By suitable arrangement of the switching element, an operating element of the switching element is accessible. During displacement of connection element 16 from the mounting position into the operating position, the locking pin is displaced against the spring force of the compression spring in the direction within outside wall 22 of pump housing 2; by the action of stop surface 17. During this movement, the operating element of the switching element is operated. As soon as the operating position is achieved, the locking pin will fall into a cutout with a blocking surface 19 and thus into its locking position. Thereby the hose 4 is held in the operating position against its internal elastic forces. It is important in this context that the locking pin will additionally hit on a ground of the cutout, the arrangement of the switching element, the length of the locking pin and the arrangement of the ground being selected such that the operating element will remain actuated in the locking position of the locking pin. As a result, by the switching element, the operation of the roller wheel 6 is only possible in the operating position of hose leg 10. From FIG. 1 can be seen that the second hose leg 9 is fixed in the longitudinal direction of hose 4. In the frame of fixed hose leg 9 there is configured a connection element 12 having stop surfaces 13 extending orthogonally to the longitudinal extension of hose 4. The stop surfaces 13 run up against the fixing surfaces 14 in cassette housing 2. In the frame of connection element 12 of the fixed hose leg 9 there is provided a pressure sensor 15 communicating with the peristaltic pump 2, when cassette 1 is mounted at peristaltic pump 2. In the shown embodiment, a pressure sensor 15 is adapted as a pressure membrane 15 of a pressure chamber, and at the pump housing 21 there is mounted a pressure transducer 25 such that pressure membrane 15 rests against the pressure transducer 25, when cassette 1 is mounted (see also FIG. 2). From FIG. 1 it can be seen that the hose 4 including connection elements 12, 16 can be removed from the cassette housing 3. Removal is achieved in the direction approximately orthogonal towards a top of the paper plane in the shown view.

The hose 4 consists in the area of the circular segment or between connection elements 12, 16 of a rubber-elastic material, namely silicone caoutchouc. The hose 4 may, adjacent to the connection elements 12, 16 be made from an identical or a different material. In particular, it is possible to use non-rubber-elastic materials, too.

Figure 2:
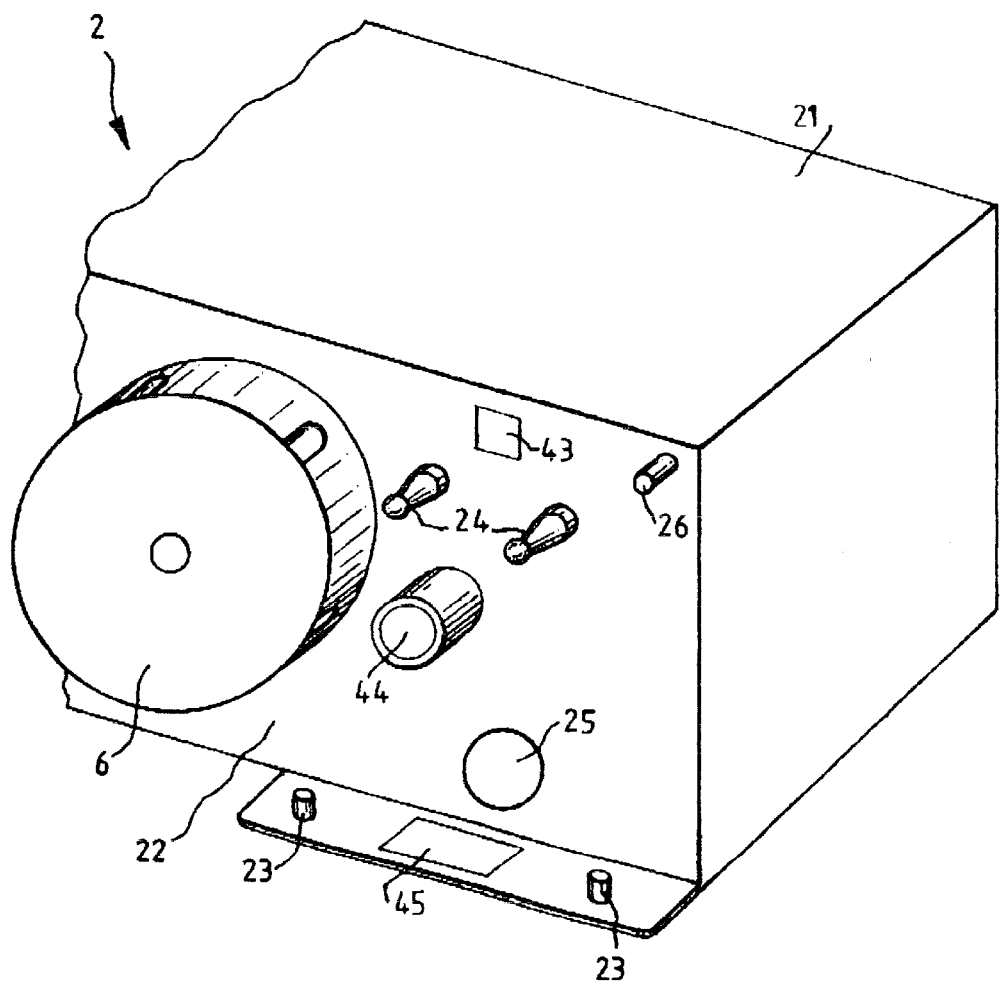
FIG. 2 is a view of a device for which the subject matter of FIG. 1 is intended.

By comparing FIGS. 1 and 2, the means for fixing hose cassette 1 to peristaltic pump 1 can be seen. In FIG. 1 it is visible that at a wall 20 being orthogonal to the half-oval surfaces, two positive-drive cutouts 7 are provided, and that spaced with respect to positive-drive cutouts 7, in relation to wall 20, two friction-drive connection elements 8 are provided. In the frame of the peristaltic pump 2, complementary connection elements 23, 24 are arranged. Connection elements 23 are holding pins 23 positively engaging into positive-drive cutouts 7. Friction-drive connection elements 8 and complementary connection fittings 24 are adapted as a releasable friction-drive connection. For mounting hose cassette 1 at peristaltic pump 2, first positive-drive element cutouts 7 are positioned on holding pins 23 and are slid on, hose cassette 1 being held in a tilted manner with respect to outside wall 22. It is understood that between positive-drive cutouts 7 and holding pins 23 a sufficient clearance is provided. After mounting, hose cassette 1 is tilted against outside wall 22 and is pressed against this outside wall 22, thus the connection between friction-drive connection elements 8 and connection fittings 24 being established, and hose cassette 1 being held at peristaltic pump 2. The removal is achieved in reversed sequence. In the shown embodiment, the hose 4 operates as a rinsing line. The hose 4 may however also operate as a sucking line. Further, it is possible, irrespective of the shown embodiment, that a second hose is provided in the frame of the cassette 1, for instance operating as a discharge line, and shutter means may be provided in the frame of the peristaltic pump. Such a means blocks the second hose when the cassette is mounted. In the embodiment of FIG. 1, a cassette chamber 32 is provided for this purpose. For further details, explicit reference is made to patent application DE-199 60 668.

In FIG. 1 various embodiments of storage units can further be seen, namely a magnetic tape 40, a micro-chip 41, and a transponder 42. FIG. 2 shows the respectively assigned readout units, namely a magnetic tape reader 43 for magnetic tape 40, a device 44 for contacting the micro-chip 41, and a transponder scanning transceiver 45 for information exchange with the transponder 42. The information exchange with the transponder 42 takes place in an inductive manner. It is understood that the respectively corresponding components are positioned in hose cassette 1 and at peristaltic pump 2 such that readout unit and storage unit can communicate with each other in the desired way. When connection element 16 is moved from its mounting position into its operating position, magnetic tape 40 is pulled past magnetic tape reader 43, so that its identification information is read out. The micro-chip 41 is contacted when hose cassette 1 is mounted. The transponder 42 is brought close to transponder scanning transceiver 45, when hose cassette 1 is mounted, so that the power required for operating transponder 42 is also transmitted inductively. For the alternative case of micro-chip 41 and the transponder 42, a readout is performed by the actuation of switching element 26. Program sequences according to the invention, for instance an activation of the readout unit for reading out the identification information, are initiated.

It is understood that the variants of storage units described above in a hose cassette 1 with the respective readout units are shown for simplicity reasons only in an individual hose cassette or an individual peristaltic pump 2. One variant will normally be fully sufficient for carrying-out the invention.

Figure 3:
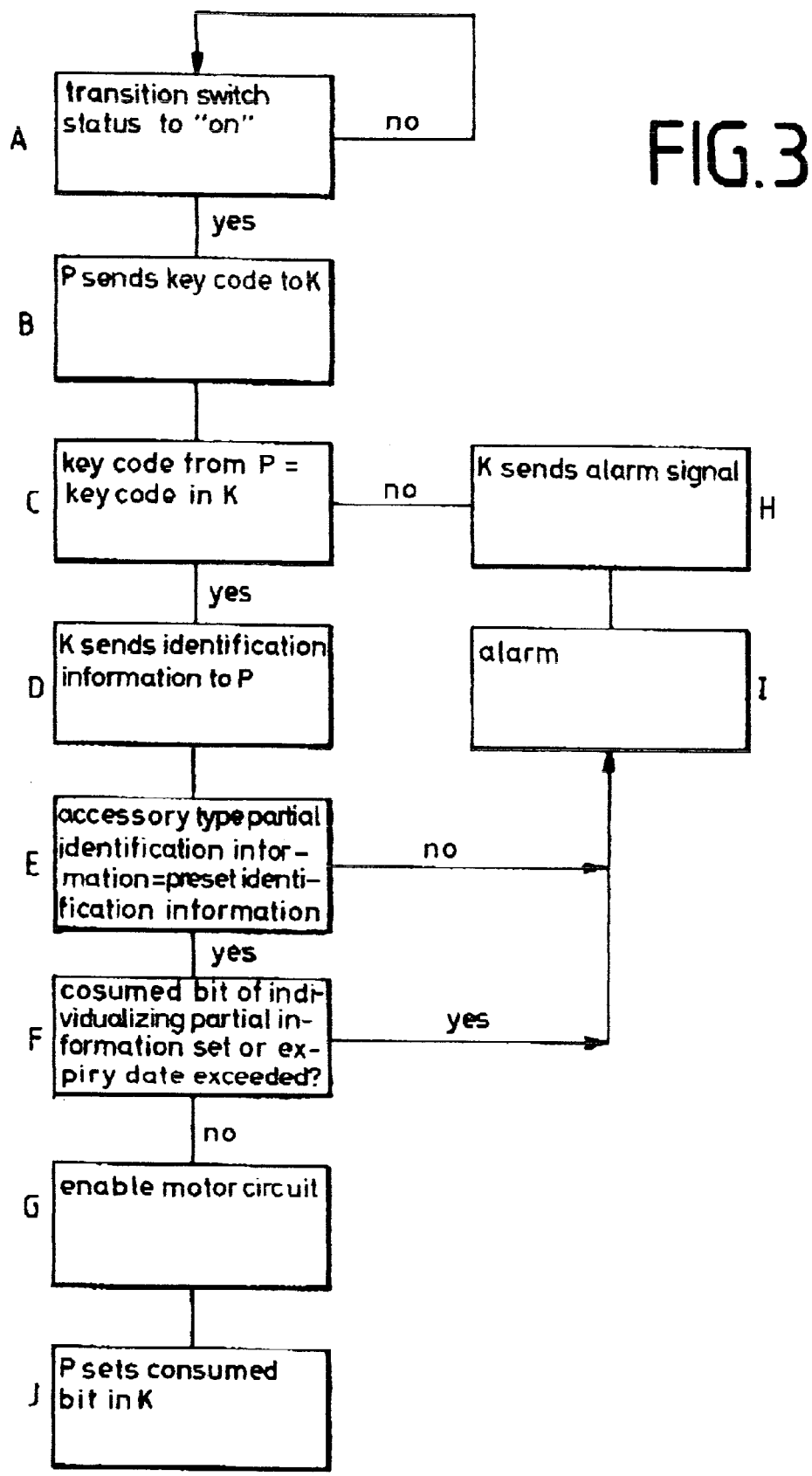
FIG. 3 is a flow diagram for a method according to the invention.

When hose cassette 1 is connected to the peristaltic pump 2 and the described sequences are initiated, the routines according to FIG. 3 are started. Initially, the program checks in the readout unit (43, 44 or 45) of pump 2, whether switching element 26 signals a transient to "on", because of the mounting and tensioning of hose cassette 1. As soon as such transient is detected, readout unit (43, 44 or 45) will transmit a key code to storage unit (40, 41 or 42) of cassette 1. In the storage unit (40, 41 or 42) the received key code is compared to the stored key code. When there is no match, the storage unit (40, 41 or 42) sends an alarm signal to the readout unit (43, 44 or 45), with the consequence that readout unit (43, 44 or 45) generates an alarm of peristaltic pump 2. When there is a match, the storage unit (40, 41 or 42) transmits the stored identification information to the readout unit (43, 44 or 45). The readout unit (43, 44 or 45) then compares the accessory piece type information contained in the identification information to a list of allowed accessory piece type information stored in the readout unit (43, 44 or 45). When there is no match, the readout unit (43, 44 or 45) activates an alarm of peristaltic pump 2. When there is a match, it is verified in the readout unit (43, 44 or 45) whether a consumed bit being part of the individualizing piece information (part of the identification information transmitted already) has been set or whether an expiry date, again being part of the individualizing piece information, has been exceeded. For doing the latter, the readout unit comprises a real time clock with date function. If one of the conditions is met, the alarm will be activated. If none of the conditions are met, the motor control is enabled for being activated by an operator. This enable condition is maintained till a de-activation of the motor control by an operator or by a transient of switching element 26 to "off". After enabling, the readout unit (43, 44 or 45) will transmit a signal, by which the consumed bit in the storage unit is set. As a result, no unauthorized accessory piece can be used, and even already used or aged authorized accessory pieces are excluded from use. The functions A, B, E, F, G, I, and J are (in part) implemented in the software of the readout unit (43, 44 or 45). The functions C, D, H, and J are (in part) implemented in the software of the storage unit.

While specific embodiments of the invention have been shown and described in detail to illustrate the application of the principles of the invention, it will be understood that the invention may be embodied otherwise without departing from such principles.

What is claimed is:

1. A medical device comprising a medical apparatus comprising an accessory port, and at least one accessory piece comprising a connection element being complementary to said accessory port, the connection element comprising a storage unit wherein coded identification information is stored, wherein, if the accessory piece is connected to the device, coded or un-coded identification information is readable from the storage unit by means of a readout unit located at or in the vicinity of said accessory port and, in the case of reading coded identification information that is de-codable, read-out and de-coded identification information is compared to preset valid identification information stored in readout unit, and wherein the medical device is activated if the identification information is at last partly matching the preset valid identification information, and is blocked if the identification information does not match, and wherein coded identification information is de-coded by means of a proprietary key code prior to comparison with the preset valid identification information.

2. A device according to claim 1, wherein decoding of identification information is achieved by the readout unit transmitting the key code to the storage unit, and that storage unit enabling the identification information in an un-coded manner for readout, if the transmitted key code matches a key code stored in the storage unit.

3. A device according to claim 1, wherein decoding of identification information is achieved by that readout unit transmitting the key code to the storage unit and that in the storage unit a transformation of the coded identification information into un-coded identification information is performed by means of the key code.

4. A device according to claim 1, wherein decoding of identification information is achieved by the coded identification information being read out from storage unit, and in readout unit a transformation of the coded identification information into un-coded identification information is performed by means of the key code.

5. A device according to claim 1, wherein the key code is selected from the group including a fixed code, a changing code, a sequential changing code, a stochastic changing code, and combination a fixed code, a changing code, a sequential changing code, a stochastic changing code.

6. A device according to claim 1, wherein the storage unit includes a transponder and the readout unit includes a transponder scanning transceiver.

7. A device according to claim 6, wherein a transmission of information between the transponder and the transponder scanning transceiver takes place by mans of electro-magnetic waves or inductively or capacitively or galvanically.

8. A device according to claim 5, wherein, with the transmission of information from transponder scanning transceiver to the transponder, the power required for operating transponder is also transmitted.

9. A device according to claim 1, wherein the storage unit is configured as a passive storage unit with a magnetic strip.

10. A device according to claim 1, wherein the medical apparatus is a sucking and/or rinsing pump or a gas supply system for the fields arthroscopy, dialysis, hyteroscopy, cystoscopy, laparoscopy and breathing technologies, wherein the accessory piece is a hose set for the connection of the medical device to a medical instrument.

11. A medical device comprising:

a medical apparatus with an accessory connection;

an accessory piece with a connection element complementary to said accessory connection;

a code storage associated with said accessory piece, said code storage having a code stored therein;

a readout unit located at or in the vicinity of said accessory connection, said readout unit reading a code from said code storage unit;

a code de-encryption device and control connected to one of said readout unit and said storage unit for de-encryption of the code stored in said storage unit based on de-encryption key and for comparing the de-encryption of the code with preset valid information and for sending at least one of a blocking or unblocking signal depending upon the result of the comparing of the de-encryption of the code with the preset valid information;

an operative device associated with one of said medical apparatus and said accessory connection for responding to said blocking or unblocking signal to prevent the accessory piece or medical apparatus from operating where the compared de-encryption of the code and the preset valid information do not provide a preset result.

12. A device according to claim 11, wherein the de-encryption key is stored in the storage unit with the stored code.

13. A device according to claim 11, wherein de-encryption of the stored code occurs after reading out the encrypted code from the storage unit, and in the readout unit the encrypted code is de-encrypted.

14. A method for operating a medical device including a medical apparatus with an accessory connection part and an accessory piece that is complementary to the accessory connection part, the method comprising:

providing the accessory piece with a storage unit having a code;

providing the accessory connection part with a read out device;

providing a control unit operatively connected to the medical apparatus or the accessory piece for enabling operation or disabling operation of one or more of the medical apparatus and the accessory piece;

providing a decoder for decoding the stored code based on a code key;

de-coding the stored code using the code key and the decoder; and controlling the operation with the control unit based on the decoding, wherein the code is one of stored in the storage unit or is associated with the decoder.

15. A method for operating a device according to claim 14, the method comprising:

in the case of reading coded identification information that is de-codable, comparing read-out and de-coded identification information to preset valid identification information stored in readout unit;

activating the medical device if the identification information is at last partly matching the preset valid identification information;

blocking the medical device if the identification information does not match;

de-coding a coded identification information using a proprietary key code prior to comparison with the preset valid identification information.

16. A method according to claim 15, further comprising providing a program coding for the functions of the storage unit.

17. A method according to claim 15, further comprising providing a program coding for the functions of the readout unit.

* * * * *